(12) United States Patent
Rinecker

(10) Patent No.: US 8,792,615 B2
(45) Date of Patent: Jul. 29, 2014

(54) METHOD FOR IDENTIFYING POSSIBLE CHANGES IN THE RANGE OF A PLANNED IRRADIATION FIELD BEFORE THE PATIENT IS IRRADIATED WITH CHARGED PARTICLES

(76) Inventor: Hans Rinecker, Munich (DE)

(*) Notice: Subject to any disclaimer, the term of this patent is extended or adjusted under 35 U.S.C. 154(b) by 355 days.

(21) Appl. No.: 13/370,534

(22) Filed: Feb. 10, 2012

(65) Prior Publication Data

US 2012/0205557 A1     Aug. 16, 2012

(30) Foreign Application Priority Data

Feb. 11, 2011 (EP) .................................. 11154210

(51) Int. Cl.
*A61N 5/10* (2006.01)

(52) U.S. Cl.
USPC ............................................................ 378/65

(58) Field of Classification Search
USPC ............ 378/62, 65, 98.11, 98.12; 250/492.3, 250/492.1
See application file for complete search history.

(56) References Cited

U.S. PATENT DOCUMENTS

2007/0164230 A1    7/2007   Rigney et al.

FOREIGN PATENT DOCUMENTS

| EP | 1 380 262 | 1/2004 |
|----|-----------|--------|
| EP | 1 911 493 | 4/2008 |
| EP | 2 229 981 | 9/2012 |

*Primary Examiner* — Courtney Thomas
(74) *Attorney, Agent, or Firm* — Cozen O'Connor

(57) ABSTRACT

A method serves as a supplemental safety mechanism before the irradiation of a patient with charged particles. By this method, differences which occur from day to day in the density composition within the patient are found, and the influence on the range of the planned irradiation field is determined. For this purpose, two high-resolution x-ray detectors are required, which form an angle of 60-120° to each other.

16 Claims, 16 Drawing Sheets

| 5 | 6 | 5 | 4 | 3 | 6 |
|---|---|---|---|---|---|
| 4 | 3 | 6 | 5 | 4 | 5 |
| 5 | 6 | 5 | 4 | 6 | 3 |
| 5 | 7 | 4 | 3 | 5 | 6 |
| 6 | 5 | 5 | 4 | 6 | 5 |

Fig. 11(a)

Nominal x-ray image

| 5 | 5 | 4 | 6 | 4 | 5 |
|---|---|---|---|---|---|
| 4 | 5 | 6 | 5 | 4 | 6 |
| 5 | 29 | 35 | 37 | 33 | 6 |
| 6 | 30 | 32 | 34 | 35 | 33 |
| 7 | 35 | 33 | 36 | 6 | 5 |

Fig. 11(b)

Actual x-ray image

| 0 | -1 | -1 | 2 | 1 | -1 |
|---|---|---|---|---|---|
| 0 | 2 | 0 | 0 | 0 | 1 |
| 0 | 23 | 30 | 33 | 27 | 3 |
| 1 | 23 | 28 | 31 | 30 | 27 |
| 1 | 30 | 28 | 32 | 0 | 0 |

Fig. 11(c)

Difference image
    Actual x-ray image
    minus Nominal x-ray image

|  | I | II | III | IV |
| --- | --- | --- | --- | --- |
| left difference image | X | X | O | O |
| right difference image | X | O | O | X |

METHOD FOR IDENTIFYING POSSIBLE CHANGES IN THE RANGE OF A PLANNED IRRADIATION FIELD BEFORE THE PATIENT IS IRRADIATED WITH CHARGED PARTICLES

BACKGROUND OF THE INVENTION

Field of the Invention

The present invention relates to a method for identifying possible changes in the range of a planned irradiation field before the patient is irradiated with charged particles.

In comparison with conventional irradiation systems which work with x-rays or photon beams, systems for irradiating patients with charged particles offer considerable advantages with respect to the accuracy of dose administration and the extent of the side effects on healthy tissue.

Conventional photon beams penetrate the body, but they are also absorbed during their interaction with the molecules of the body and thus steadily lose their intensity. The maximum dose lies just under the skin, as can be seen from dose distribution curve A in FIG. 1. This effect is based on the recruitment of stray radiation, which starts immediately under the skin. As it travels further toward the tumor area Z, the radiation dose decreases in the form of an exponential curve. A tumor lying deep in the body thus receives a weaker dose than healthy tissue in the path of the beam in front of the tumor, whereas organs lying behind the tumor still receive a considerable dose.

In contrast, charged particles such as protons and heavy ions initially lose only a relatively small amount of their energy after entering the body, but they are decelerated by repeated interaction with matter (see FIG. 2). The more the particles slow down, the larger the amount of energy they release and the more they are decelerated. This leads to an "energy explosion" at the end of the particle path, the so-called "Bragg peak" (dose distribution curve B in FIG. 2). The dose delivered in front of the tumor by charged particles is much lower than that of irradiation with photons, and at the same time the dose is concentrated in the tumor. The limited, defined range of a proton beam means that the dose decreases very sharply after the Bragg peak. In the case of proton irradiation, therefore, the area of the patient behind the tumor is exposed to no radiation at all. The ability to control the velocity of the particles and to deflect them laterally at the same time therefore makes it possible to target the dose 3-dimensionally into the tumor. By varying the particle velocity, furthermore, the radiation can also be moved across the tumor in the depthwise direction, as can be seen from the Bragg plateau C shown in FIG. 3.

A preferred method is the so-called grid-scan method, in which the Bragg peak of the beam of charged particles travels across the tumor with millimeter accuracy under computer control in a 3-dimensional grid determined beforehand by diagnostic procedures and irradiation planning. In this method, the beam typically has a diameter of 7-10 mm FWHM, and the individual grid points (of which there are typically a few hundred to a few thousand) are targeted one after the other. During a radiation session, each point is exposed to the dose calculated for the individual case. A patient is usually treated over the course of several irradiation sessions on successive days.

Irradiation with charged particles represents a considerable advance in cancer treatment especially in cases where the tumors are located near vital healthy structures or are very deep and cannot be treated by photon beam therapy at all in many cases or only at high risk because of the unavoidable and undesirable damage to healthy tissue.

In radiation with charged particles according to the grid-scan method, the dose distribution achieved with the pencil-like beam is sharp and concentrated, as previously explained. Although this makes it possible to achieve highly precise targeting in three dimensions, it is also associated with very high requirements on accuracy.

In the following, this should be explained in more detail on the example of proton therapy. The range of a proton beam depends not only on the initial energy at the time the beam enters the body but also on the nature of the tissue through which the proton beam passes on its way to the location where the dose is to be delivered in the body (the tumor).

When proton therapy is used, a so-called therapy plan is therefore prepared as the initial step. First, computer tomography data (CT data) of the highest possible resolution are acquired for the body areas in which an irradiation target area is located. The gray-scale values (so-called Hounsfield units) in the data are then converted to electron density values by suitable calibration of the CT scanner and finally converted into stopping power for protons. The attending radiation therapist then draws the contours of the target areas and also the contours of the critical structures and organs to be safeguarded on the sectional images thus obtained (possibly with the use of additional diagnostic modalities such as nuclear spin tomography). In this way, 3-dimensional forms are obtained by interpolation between the sectional images. In the next step, the expert in medical physics will use a computer system to produce the therapy plan, according to which the target area (tumor) will be treated with the desired dose while healthy tissue will be protected throughout the treatment.

In the case of proton therapy by the scanning method, the direction in which the protons are to travel is decided, and a 3-dimensional fluence matrix is set up, which contains the locations, energies, and dose weights of the individual beams (scanning spots). Optimization of this fluence matrix leads to the desired dose distribution (usually homogeneous) in the target area under optimal protection of the critical structures. For this purpose, the therapy planning system uses all of the information from the 3-dimensional CT data set and the drawn-in contours. This means that, for each individual beam with a given target location (lateral x and y and penetration depth z), all of the density variations such as those attributable to muscle, bone, and lung tissue are taken fully into account with respect to their ability to stop a proton beam.

The therapy plan thus prepared can now be applied to the patient. The indispensable prerequisite for a successful treatment is first that the position of the patient be maintained correctly during each irradiation session. For this purpose there are many approaches to a solution, including vacuum mattresses, bite blocks, immobilization masks, and x-ray system-supported position verification systems.

Safety devices also check the therapy planning data and the functionality of the system to minimize the chance that the therapy planning data could be implemented incorrectly or that data transmission errors could occur between the individual components of the system.

In spite of all these measures, additional factors can also affect the precision of the irradiation and thus the success of the treatment. For example, differences can occur in the density composition or in the distribution of the density compositions within the patient. These can involve, for example, gas inclusions in the intestine or fatty folds (which can occupy different positions at the surface of the patient). For a given patient position and a given therapy plan, it is therefore possible for range variations to occur for the individual beams of the therapy plan, which is based on the density distribution present during the CT imaging procedure. Under certain circumstances, such range variations can also be significant for the success of the treatment if the target volume might not be supplied homogeneously with the dose or if an area with a critical structure is exposed to an unwanted dose. Because of the steep drop in the dose in the beam direction just behind the Bragg peak, an unintended variation in the range of individual proton beams is much more important clinically than a variation in the patient geometry would be in the case of conventional radiation therapy with photon beams, the dose of which decreases in a level, exponential manner.

Most of these influences are taken into account within the scope of the therapy planning optimization process and enter into the maximization of the so-called "robustness" of the therapy plan. Because a radiation treatment, as mentioned above, is usually distributed over several therapy sessions (fractions), it is possible for variations in density and therefore in range to occur between one day and the next, and these variations must be reviewed individually.

FIGS. 4(a) and 4(b) serve to illustrate this problem. FIG. 4(a) shows again a characteristic deep dose curve of a proton beam in a homogeneous medium. The curve ends at the familiar Bragg peak at range $R_1$.

In general it is true that each high-energy proton, upon penetrating into matter, has a range which depends on its initial energy and on the density and composition distribution of the irradiated material. Because of the statistical nature of the interactions of protons with matter and thus of the energy loss process, this range is subject to fluctuation. For a proton beam with a certain initial energy, the depth-dose curve is obtained by integration of the energy losses. The stopping power dE/dx for protons in matter is sufficiently well known from the literature and is well described by the so-called Bethe-Bloch formalism.

If the density function changes in part of the irradiation path of the proton beam as the result of, for example, an air bubble (shaded area D in FIG. 4(b)), which replaces the intestinal content originally present, then what results is a change in the range. In the present example, this change takes the form of an increase in the range of the proton beam to the value $R_2$.

In principle, it would be possible to solve this problem by conducting, on each individual treatment session day, a comprehensive computer tomography followed by a complete therapy planning procedure based on that particular day's current density distribution. This is impossible, however, for several reasons. The dose loads for the patient associated with a daily computer tomography are already unacceptable by themselves. In addition, the time required for a complete computer tomography with therapy planning, even assuming optimal computer performance, takes hours and is therefore unsuitable, because the patient's density distribution could change in the meantime. Finally, in the typical case where the equipment is installed in different rooms, the need to transport the patient between the CT room and the irradiation room would again lead to uncertainties in the density distribution and thus in the range.

SUMMARY OF THE INVENTION

It is an object of the present invention to provide a method for identifying possible changes in the range of a planned irradiation field before the patient is irradiated with charged particles. The method makes it possible for the clinical user to make a rapid and transparent review of the patient's readiness for the irradiation treatment immediately before each radiation session while the patient is already in position in the treatment room, and further makes it possible to minimize the risk associated with clinically relevant range changes in parts of the treatment field in the patient which may occur between one day and the next.

According to an aspect of the invention, the method for identifying possible changes in the range of a planned irradiation field before the patient is irradiated with charged particles comprises the following steps:

conducting a computer tomography over at least a part of the patient to generate a 3-dimensional computer tomography data set;

providing an x-ray system comprising two high-resolution x-ray detectors, which form an angle of 60-120° to each other, and two x-ray sources opposite the x-ray detectors, wherein each combination of an x-ray source and an x-ray detector defines one of two projection directions;

preparing two actual x-ray images of at least a part of the patient in the two projection directions by means of the two x-ray detectors;

calculating two digitally reconstructed nominal x-ray images from the computer tomography data set corresponding to the two projection directions of the x-ray system;

conducting a difference analysis to determine differences between the actual x-ray image and the associated nominal x-ray image for the two projection directions;

checking the relevance of the found differences with respect to spatial extent and with respect to localization in reference to the planned irradiation field and determining relevant 2-dimensional areas of variation;

determining a 3-dimensional body of variation by back-projecting the two 2-dimensional areas of variation into the 3-dimensional computer tomography data set;

calculating a mean electron density of the 3-dimensional body of variation on the basis of the found differences between the actual x-ray image and the associated nominal x-ray image for the two projection directions;

identifying individual beams of the planned irradiation field which pass through the 3-dimensional body of variation;

calculating, under consideration of the changed electron density value in the 3-dimensional body of variation, prospective changed ranges of the identified individual beams of the planned irradiation field; and displaying or making available information on the calculated changed ranges.

With this method, even quickly occurring density fluctuations in the beam path can be studied with respect to their clinical relevance, and thus an additional level of safety for the irradiation of the patient with pinpoint accuracy is introduced.

The step of conducting a difference analysis for determining differences between the actual x-ray image and associated nominal x-ray image preferably comprises the step of subtracting the numerical gray-scale values of the pixels of the nominal x-ray image from those of the corresponding pixels of the actual x-ray image to determine the pixel-by-pixel deviation between the gray-scale values. In this way, it becomes possible to evaluate the differences with a high degree of detail.

Before the step of pixel-by-pixel subtraction of the numerical gray-scale values, it is preferable to adjust the gray-scale values of the actual x-ray images to match those of the nominal x-ray images, so that any system-caused gray-scale shift between the actual and the nominal x-ray images, which may be attributable to differences between the recording modalities of the actual x-ray images and the modalities of the calculation of the nominal x-ray images from the CT data set, is eliminated prior to obtaining the differences.

The adjustment of the gray-scale values between the actual and the nominal x-ray images preferably comprises the step of applying, in an iterative numerical optimization process, a matching function for matching a gray-scale value frequency curve of the actual x-ray image to a gray-scale value frequency curve of the nominal x-ray image. In this way, system-caused differences between the actual and the nominal x-ray images can be masked out reliably and efficiently.

Before the gray-scale value matching between the actual and the nominal x-ray images is carried out, it is preferable to enhance the degree of detail of the data obtained by increasing the resolution of the image with the lower resolution to match the higher resolution of the other image.

When the relevant 2-dimensional areas of variation are being determined, it is preferable to take into consideration only those areas which consist of a predetermined minimum number of connected pixels which, after subtraction, show a gray-scale value deviation above a predetermined threshold value. In this way, the information from individual pixels which may have been corrupted and noise artifacts are excluded from the method steps following thereafter.

To simplify the further calculation steps, the gray-scale values are preferably averaged over the pixels of each relevant two-dimensional area of variation.

To allow the clinical user to assess the situation immediately, each relevant 2-dimensional area of variation is preferably highlighted graphically in the actual x-ray images or in the nominal x-ray images.

Before the relevant 2-dimensional areas of variation are back-projected into the 3-dimensional computer tomography data set, the 2-dimensional areas of variation are preferably simplified into rectangles with the average width and the average length of the associated 2-dimensional area of variation. This measure makes it possible for the computerized back-projection into the 3-dimensional computer tomography data set to be carried out much more quickly.

For the calculation of the average electron density of the 3-dimensional body of variation, systems of equations are preferably solved numerically for each of the two projection directions on the basis of the x-ray attenuation relationship:

$$G(r)=e^{-\alpha \cdot \rho \cdot r}$$

wherein G is the numerical gray-scale value, and ρ is the electron density. By the use of this method, it is possible in a very simple way to obtain an approximation of the average electron density in the body of variation.

Calculating the prospective changed ranges of the identified individual beams of the planned irradiation field preferably comprises the steps of determining the differential energy loss along the penetration path of the individual beam and determining the range of the penetration path of the individual beam by integration over the energy-dependent differential energy loss. Thus the changed ranges can be effectively calculated in an approximate manner.

To accelerate the calculation procedure, it is also helpful to limit the calculation of the changed ranges of the identified individual beams of the planned irradiation field only to those individual beams with the longest original ranges. The clinical relevance of the method remains unaffected, because the individual beams with the longest original ranges are the ones which deliver the largest amount of energy and are also the ones which form the rear boundary of the irradiation field.

The presentation of information on the calculated changed ranges preferably comprises the step of displaying the information visually in the actual or nominal x-ray images as data on the extent of the range changes. Thus the clinical user obtains valuable information quickly on the clinical relevance of the density variation.

In a more complex level of the system, the presentation of information on the calculated changed ranges can comprise the step of marking or labeling a range variation in color in the distal terminal area of the irradiation field in the actual or nominal x-ray images. This makes the relevance of the density deviation even more visually accessible.

For further clarification of the clinical relevance of the density deviation, finally, in an even more complex level of the system, the presentation of information on the calculated changed ranges can comprise the step of calculating the change in the dose distribution which follows from the calculated changed ranges and the step of displaying projections of isodose areas of the changed dose distribution in the two actual or nominal x-ray images.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Additional features and advantages of the present invention can be derived from the following description, which refers to the drawings:

FIGS. 11(a)-11(c) show in schematic fashion the basic principles of obtaining the pixel-by-pixel differences between the numerical gray-scale values of the actual x-ray image and those of the associated nominal x-ray image;

DETAILED DESCRIPTION OF THE PREFERRED EMBODIMENTS

Figure 1:
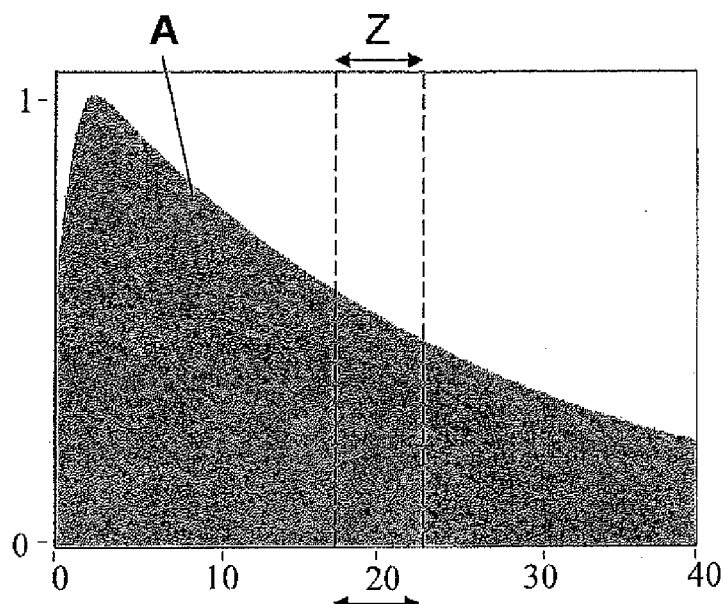
FIG. 1 shows a dose distribution curve for conventional irradiation with photons.
Figure 2:
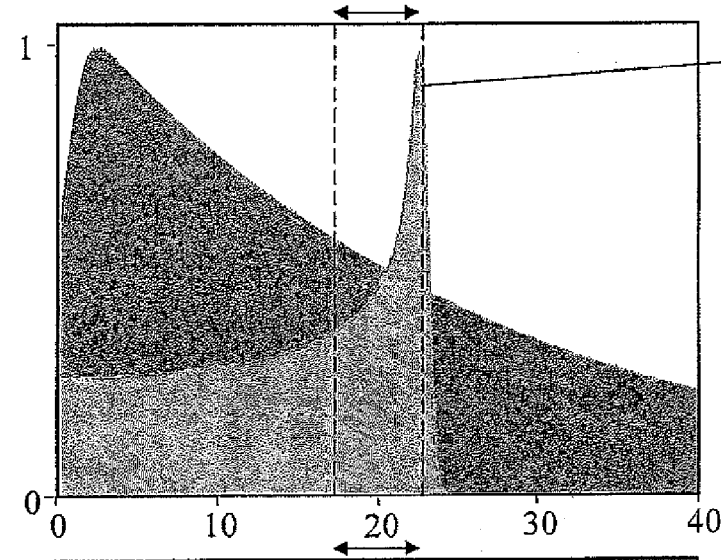
FIG. 2 shows a dose distribution curve for irradiation with protons of a certain energy in comparison with the dose distribution curve for irradiation with photons.
Figure 3:
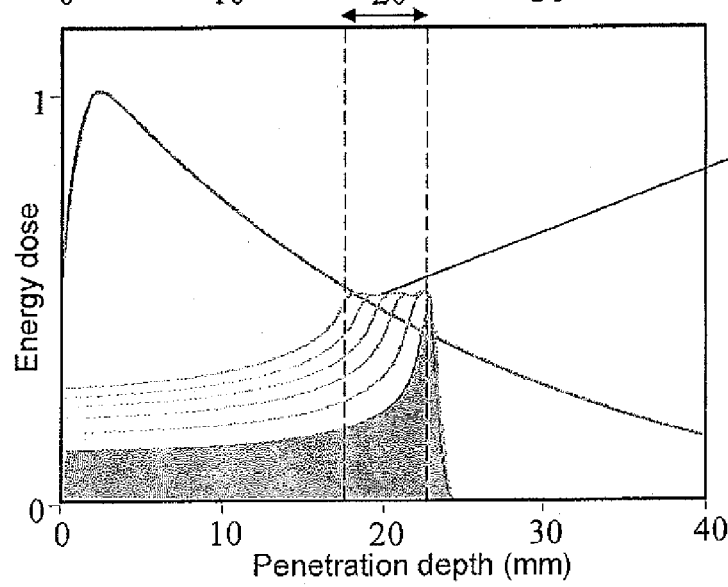
FIG. 3 shows the superimposition of various dose distribution curves for irradiation with protons for scanning the tumor.
Figure 5:
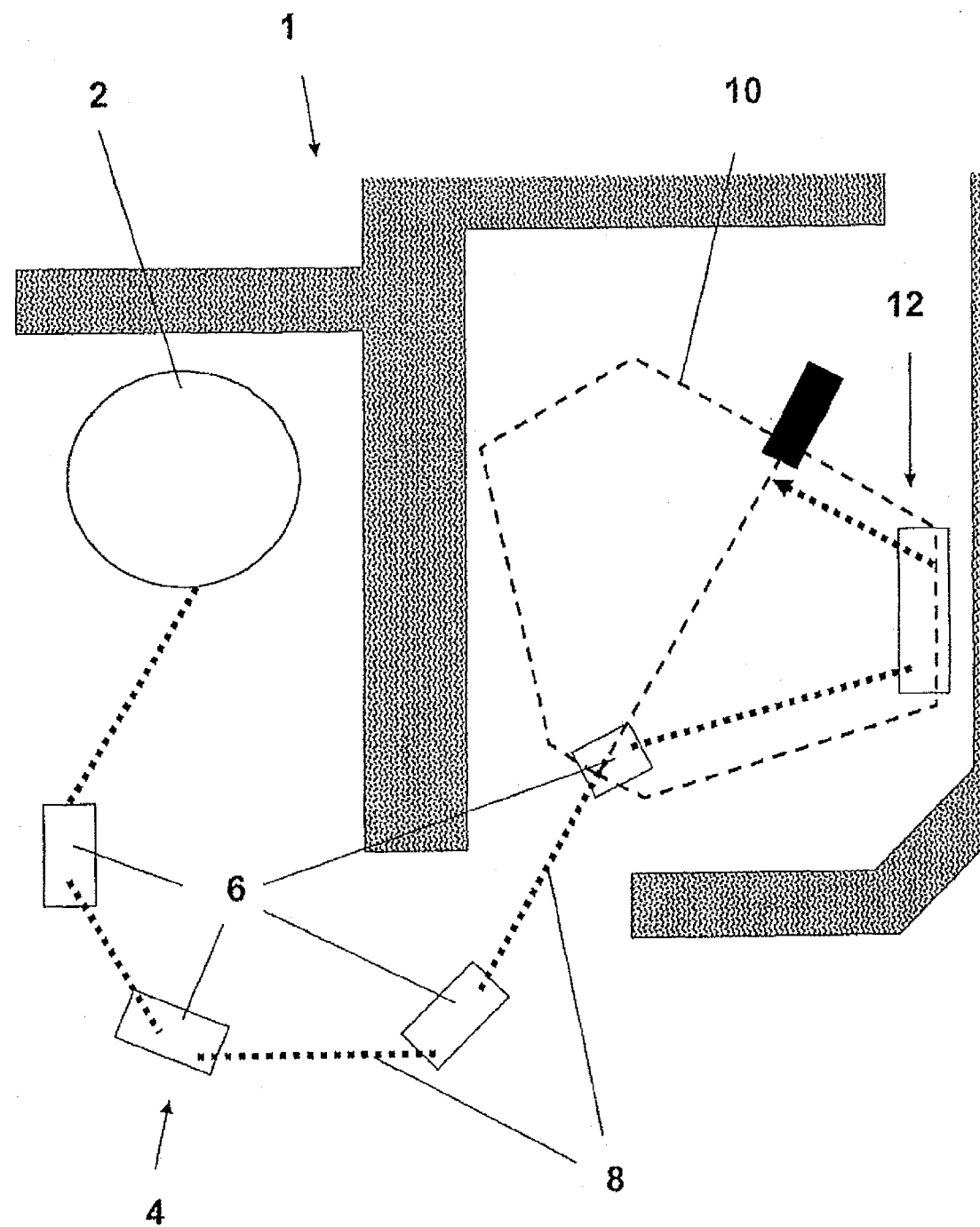
FIG. 5 is a schematic diagram of a system for irradiating patients with charged particles.
Figure 6:
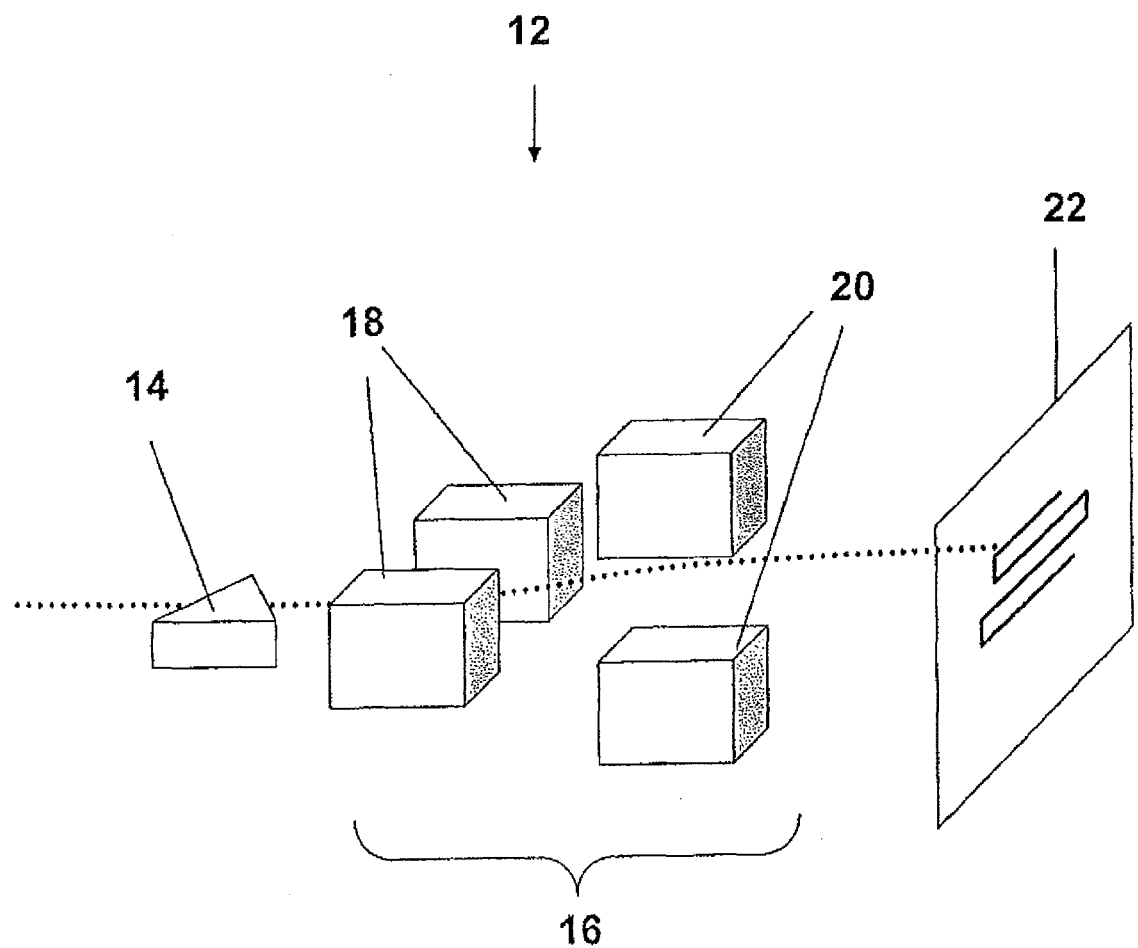
FIG. 6 is a detailed diagram of an exemplary embodiment of the 3D-scanning system.

To obtain the uniform irradiation profile of tumor tissue in the human body as shown in FIG. 3 or a profile which can be adjusted in the desired manner, the system for irradiating patients with charged particles comprises, for example, a grid-scan irradiation unit 1, which is shown schematically in FIG. 5. The grid-scan irradiation unit 1 comprises a particle accelerator 2 for charged particles. The charged particles which can be used to irradiate tumors can be, for example, protons or heavy ions. The grid-scan irradiation unit 1 also comprises a beam guide unit 4, which consists of several beam guide magnets 6 and beam guide sections 8, which are usually straight and extend between the magnets. The exact guidance of the beam is one of the most important challenges when irradiating with charged particles. The particle beam is conducted by the beam guide unit 4 into a treatment room, in which, in the case of the present example, a gantry 10 is arranged, which can be rotated around 360°. The 3D-scanning system 12 serves to irradiate the tumor tissue accurately and comprises various elements for detailed control of the particle beam, which will be described in greater detail below with reference to FIG. 6.

In the example shown here, the deflecting unit 14, 16 of the 3D-scanning system 12 is connected to the ring of the gantry 10 and can be rotated with it into any desired position, from which the patient will then be irradiated. Irradiation can thus be performed from various directions for various applications. The invention can also be applied to stationary irradiation apparatuses not designed as a gantry 10, however.

With this system, the patients are preferably irradiated by the grid-scan method, according to which the tumor tissue is subdivided into uniformly spaced grid points in a 3-dimensional grid, to which the dose is administered.

To scan the tumor with the treatment beam in a targeted manner, i.e., to target the individual 3D grid points in the target volume accurately, the 3D-scanning system 12 (see FIG. 6) has, first, an energy variation unit 14 for setting the energy of the particle beam and thus the penetration depth of the beam into the patient in the beam travel direction. In the present example, the energy variation unit 14 is designed as a degrader wedge, which can be pushed a certain distance into the path of the beam, where it will then absorb a certain portion of the energy of the particle beam. In this way, the energy of the particle beam and thus the penetration depth of the particle beam in the beam direction into the body can be controlled with sub-millimeter accuracy. In addition to the degrader wedge, other energy variation units 14 are also conceivable such as range shifter plates.

Within each layer 22 of a given penetration depth in the patient, which is defined by the energy variation unit 14 and oriented transversely to the beam direction, the particle beam can be controlled by means of a deflecting unit 16. The deflecting unit 16 comprises, for example, a double-pole deflecting magnet 18 to deflect the particle beam in the x direction and a double-pole deflecting magnet 20 to deflect the particle beam in the y direction. Other designs are also possible. The deflecting unit 16 thus generates a meandering profile of the particle beam in each layer 22 of predetermined penetration depth. To ensure a precise dose administration, the particle beam can remain turned off between one grid point and the next, depending on the distance between the points, and be turned back on again and fired onto the tumor only after the deflecting magnets 18, 20 have been reset. The dose, i.e., the number of charged particles to be administered, to adjacent grid points can vary considerably, depending on the shape of the tumor.

Figure 7:
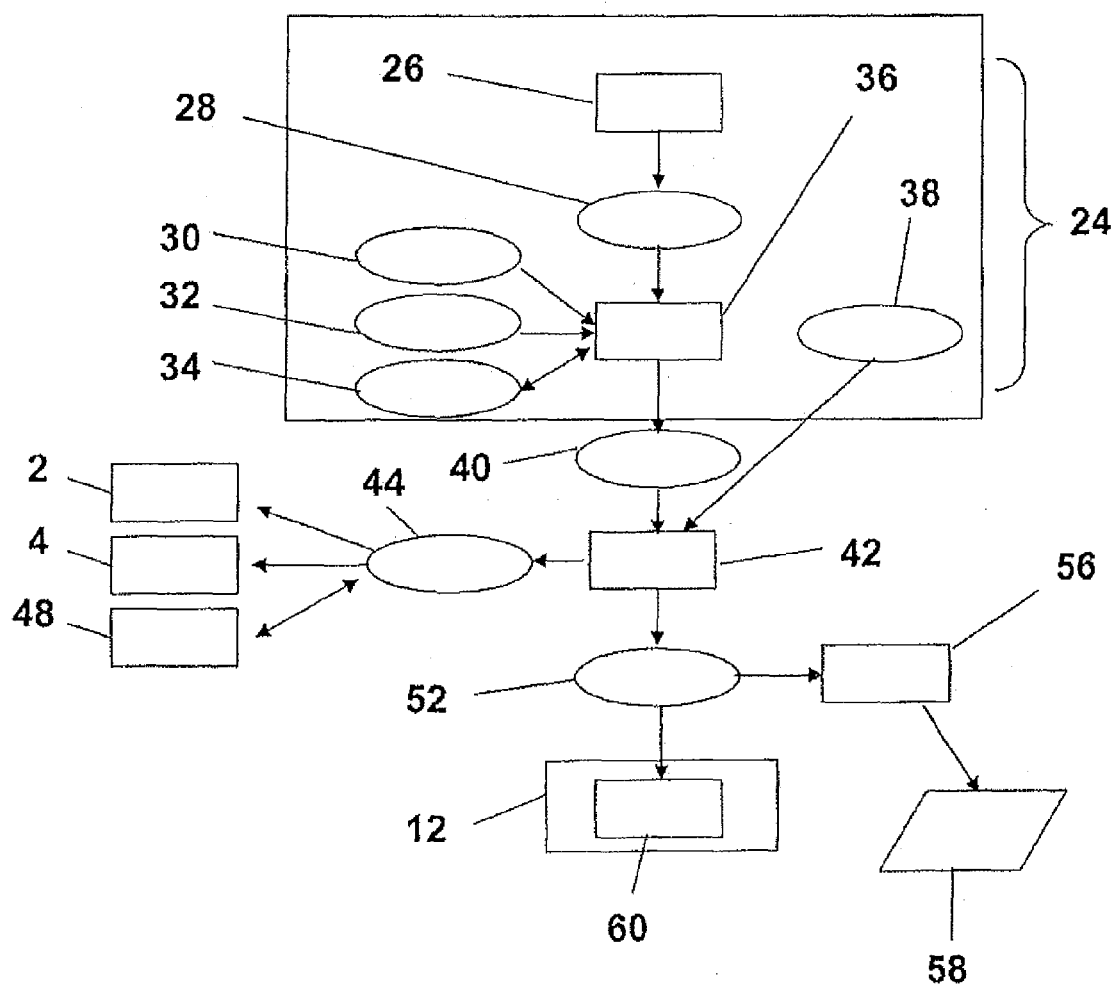
FIG. 7 is a schematic overview of the electronic components of a system which participate in the calculation and transmission of irradiation data and irradiation commands.

A highly complex system is provided for therapy planning and for ensuring that the irradiation is administered accurately. This system establishes the individual irradiation parameters down to the smallest detail and monitors the functionality of the system. The electronic components of a system which participate in the calculation and transmission of irradiation data and irradiation commands are shown in FIG. 7. The therapy planning system 24 comprises a therapy planning stage 26 for dose calculation and optimization. As explained above, all of the results of the previously conducted medical evaluation, the diagnosis, the contouring of the target volume, and the therapy concept as well as the associated CT data enter into this planning stage. On the basis of all this information, the therapy planning stage 26 calculates first the desired dose distribution (x, y, z, dose) under consideration of the parameters established by the attending physician. Then, under inclusion of the functional data of the overall system, a therapy plan 28 is generated, which determines the energy calculated from the desired dose distribution and also the number of charged particles per individual beam in each layer 22. Thus a set of data of the form {x, y, energy of the particles, number of particles} is assigned to each individual beam. These data of the therapy plan 28 are transmitted to, for example, a therapy data storage unit 36, which also contains all of the patient data 30 and the 3-dimensional CT data set 32. Safety devices 34, which examine the therapy plan in detail, are also provided at this point.

The therapy planning system 24 then supplies all of the therapy planning data 40 from, for example, the therapy data storage unit 36 to the therapy control system 42. Configuration data 38 of the system are also taken into account, including certain machine settings and configurations.

The therapy control system 42 converts the therapy planning data 40 generated by the therapy planning system 24 into irradiation commands 44 for the particle accelerator 2 and the beam guide unit 4. All of the machine-relevant data are also checked and monitored continuously by highly engineered safety devices 48. This extends from the monitoring of the doors to monitoring of the radiation to the checking of the sensors (not shown) which detect the treatment beam during the irradiation and which in themselves already represent an additional independent safety device.

The therapy control system 42 also converts the therapy planning data 40 generated by the therapy planning system 24 into irradiation data and irradiation commands 52 for the 3D scanning system 12. A scanning control module 60 which is able to accept the irradiation data and irradiation commands 52 sent from the therapy control system and to handle the job of actuating the components of the 3D-scanning system 12 on this basis is preferably incorporated into the 3D-scanning system 12.

Figure 8:
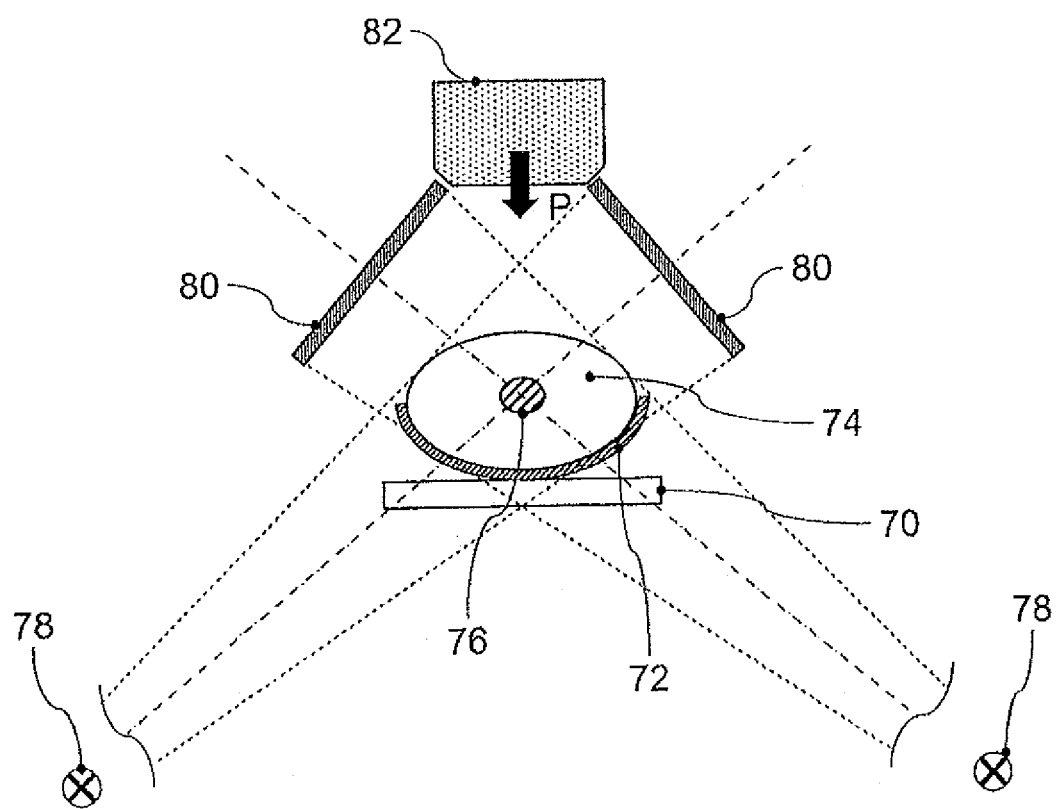
FIG. 8 is a cross-sectional schematic diagram of the arrangement of the x-ray system in the treatment room.

An arrangement of an x-ray system for the inventive method to monitor in-situ the range uncertainties in the treatment room is illustrated in FIG. 8. A vacuum mattress 72, which is prepared specifically for the patient 74 and on which the patient lies during the performance of the method and during the later irradiation treatment, rests on the patient table 70. The target area (tumor) 76 is also sketched in.

In the embodiment shown here, the x-ray system comprises two x-ray sources 78, each of which cooperates with one of the two high-resolution x-ray detectors 80 set up on the opposite side of the patient 74. This arrangement therefore defines the two projection directions. The most ergonomic and most economical approach is to perform the method with an x-ray system in which the two x-ray detectors 80 are arranged to the side of and symmetric to the proton beam direction P. In principle, the system described here can be carried out, however, with any desired angle between the x-ray detectors 80 and the proton beam direction P. The x-ray detectors 80 and the x-ray sources 78 preferably move around the patient 74 along with the rotation of the beam device 82. In fact, the x-ray detectors 80 are preferably fastened to the beam device 82. It is also conceivable in principle, however, that the x-ray detectors 80 and the x-ray sources 78 could be mounted in a stationary manner in the treatment room.

In any case it is important for the angle between the two x-ray detectors 80 to be in the range of 60-120°, and preferably in the range of 75-105°. Each x-ray detector 80 comprises at least 500×500 pixels, preferably at least 1,000×1,000 pixels, and even more preferably at least 2,000×2,000 pixels. The dimensions of the functional area of the x-ray detectors 80 should be at least 20×20 cm, preferably 30×30 cm, and more preferably 40×40 cm. Of course, rectangular x-ray detectors with sides of different length can also be used.

As a rule, two orthogonal x-ray projections are used. In more complex situations, the system described here can also provide the calculation of more than two projection directions, which increases the reliability and resolving power.

The arrangement and size of the x-ray source 78 and its x-ray detector 80 and the spacing between them should be selected so that the entire cross section of the patient is included in the projection.

First, various sets of data are made available to the system described here. All of these data can be extracted from the therapy planning data, which are generated in any case. These sets of data consist specifically of the following:

the 3-dimensional CT data set (high-resolution, layer spacing of 0.8 mm, for example), for the body region under consideration (e.g., based on DICOM, a medical standard);
 3-dimensional so-called "structure sets" (also based on DICOM) of the target area to be irradiated and of the other structures to be considered (e.g., at-risk organs, rectal ballooning, etc.), which are then also used for the projections;
 a suitable selection of isodose areas obtained from the therapy planning for the planned irradiation field; these are also made available as 3-dimensional structure sets based on DICOM; and
 a fluence matrix for the individual beams resulting from the therapy planning for the irradiation field under consideration. The matrix contains the lateral coordinates of the individual beam {x, y}, the initial energy of the individual beam (at the surface of the patient), the range of this individual beam (z direction) calculated by the planning system, and the fluence of the individual beam (i.e., the number of protons intended to contribute to the dose, typically stated in Monitor Units (MU)).

After all of the data for the current patient 74 to be treated have been loaded into the system, the first step is to position the patient 74 on the patient table 70 and then carefully to examine this position. This is done by means of an independent system (position verification system), not shown here.

Figure 9A:
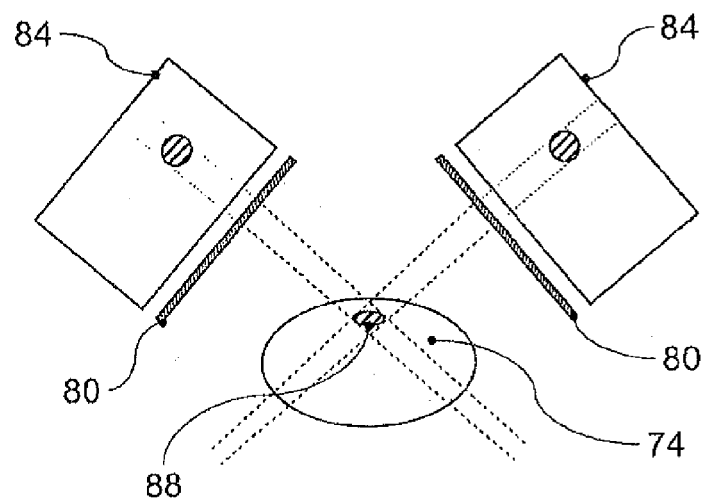
FIGS. 9(a)-9(c) are schematic diagrams of the course of the difference analysis for determining differences between the actual and the associated nominal x-ray image.
Figure 9B:
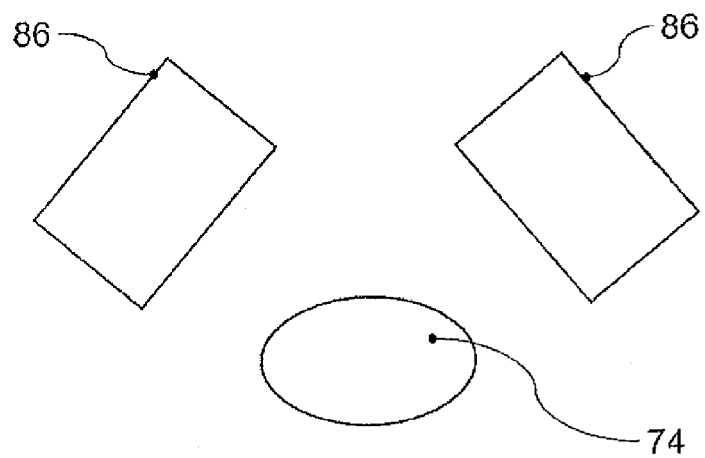
Figure 9C:
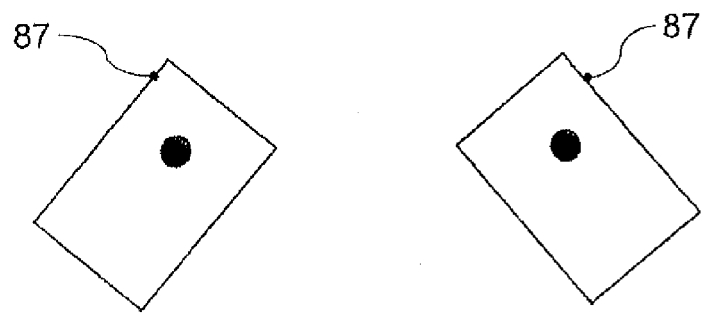

With the patient in the correct position, the x-ray system is used to record two actual x-ray images 84, that is, projection images of the relevant area of the patient 74 around the proton beam target area 76 (see FIG. 9(*a*) showing the actual x-ray images 84 of the x-ray detectors 80 flipped down in the diagram). In addition, corresponding digitally reconstructed nominal x-ray images 86 (so-called DRRs=digitally reconstructed radiographs) for the projection directions identical to those of the x-ray system are generated from the 3-dimensional CT data set 32 (see FIG. 9(*b*)). Digitally reconstructed radiographs resemble normal x-ray images but originate from the image data of computer tomography. In the computer, a virtual view of the 3-dimensional data set is calculated, wherein the voxels acquire a density-dependent transparency. The result is a summation image of a structure lying in the viewing direction. By this measure, an image with the same geometric perspective as the x-ray detector arrangement is generated from the CT data set. The image is formed by voxel summation along the divergent bundle of rays spreading out from the virtual focus to the virtual image plane. Known acquisition methods are used for this purpose.

After that, a difference analysis is carried out to find the differences between the actual x-ray image 84 and the associated nominal x-ray image 86 for the two projection directions. If there are no density variations, the actual x-ray image 84 and the associated nominal x-ray image 86 should not show any differences. In the case of a homogeneous body and a homogeneous density variation 88 as sketched schematically in FIG. 9(*a*), the difference image 87 (FIG. 9(*c*)) gives us a clear signal of the density difference.

Several preparations may have to be made before this difference analysis. If necessary, for example, the areas in the nominal x-ray images 86 and in the actual x-ray images 84 which correspond to the overlap between the two in the projection in question are selected. After that, the resolution can under certain conditions be adjusted by suitable image scaling algorithms to the higher of the two, i.e., either to the resolution of the actual x-ray images 84 or to the resolution of the nominal x-ray images 86.

In addition, it may be necessary to match the gray-scale values of the actual x-ray images 84 to those of the nominal x-ray images 86. The basic features of a gray-scale value matching procedure are shown in FIGS. 10(*a*)-10(*c*).

The starting situation in the case of a gray-scale value matching procedure is a certain gray-scale value distribution in the nominal x-ray image 86. For the same x-rayed object and the same dynamic imaging into gray-scale values, the actual x-ray image 84 will be identical to the nominal x-ray image 86. In most cases, however, there will be differences, because, for equipment-related reasons, the dynamic behavior of the x-ray system will be different from the settings of the system which created the virtual nominal x-ray image 86 from the CT data set 32. When the histograms of the gray-scale values are plotted for the nominal and actual x-ray images, the gray-scale value distributions in the histogram should be identical with respect to frequency for the same object. If the density variation 88 to be identified is not too large (for example, it should not cover the whole imaging area), then the potential differences in the gray-scale value histogram resulting from the density variation 88 can be ignored. This is true in particular because the gray-scale value distribution is dominated by anatomical structures such as bones and soft tissues. It is therefore permissible as an approximation to match the gray-scale value distribution of the actual x-ray image 84 to the gray-scale value distribution of the nominal x-ray image 86.

Figure 10A:
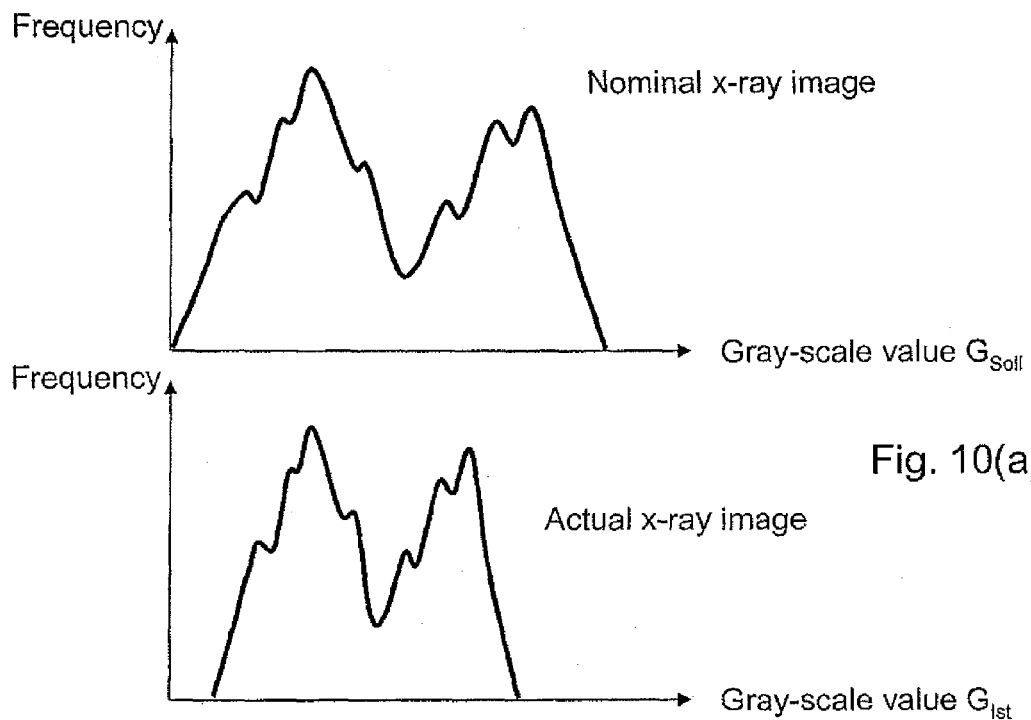
FIGS. 10(a)-10(c) show in schematic fashion the basic principles of a gray-scale value matching between the actual and the associated nominal x-ray image.
Figure 10B:
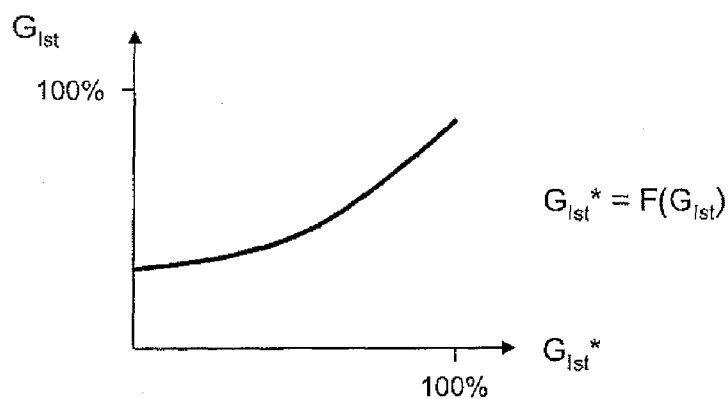
Figure 10C:
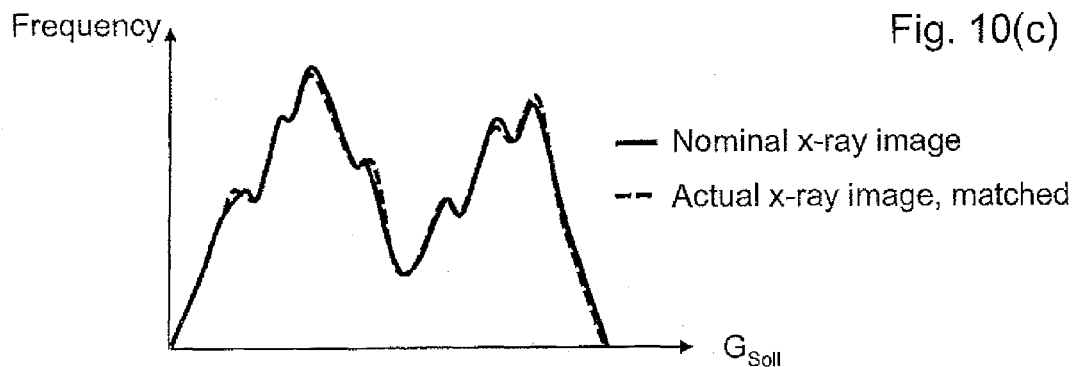

FIG. 10(a) shows the starting situation with the two gray-scale value distributions for the nominal x-ray image 86 and the actual x-ray image 84. It is shown here schematically that the actual x-ray image 84 contains the same information (form of the distribution), but also that its dynamics are different. By means of a matching function (FIG. 10(b)), the actual x-ray image 84 is now adjusted to match the nominal x-ray image 86. In the simplest case, this matching function F is a polynomial of the second degree. Depending on the type of machine being used, this second-degree polynomial could be replaced by a different function. In an iterative numerical optimization process, the determining parameters for the matching function are now obtained, so that the adjusted gray-scale value distribution of the actual x-ray image 84 agrees as closely as possible with the gray-scale value distribution of the nominal x-ray image 86 (FIG. 10(c)). Optimization is performed towards a $\chi^2$ function, which contains the difference between the two frequencies in the gray-scale value histograms for the individual gray-scale values. According to the optimization strategy, the lower degrees of the matching function are varied first, because these are the most important for the imaging of the physical differences between the actual x-ray image 84 and the nominal x-ray image 86.

Because the nominal x-ray image 86 and the actual x-ray image 84 are now present in the same resolution and in the same gray-scale value range, it is possible, as illustrated in FIGS. 11(a)-11(c), to obtain the pixel-by-pixel differences between the two sets of numerical gray-scale values. Both negative and positive gray-scale value differences can occur, depending on whether a density variation 88 with an increased density or with a decreased density in comparison to the original density distribution is present in the detected area.

In addition to the method described here, there are also other possibilities for implementing a difference analysis between the actual x-ray image 84 and the associated nominal x-ray image 86, but they will not be described in detail here.

In the next step, the goal is to check the relevance of the differences found in the difference analysis with respect to their spatial extent and localization in reference to the planned irradiation field and to determine the relevant 2-dimensional areas of variation. There are also many possibilities for doing this. An especially advantageous method is described below.

Figure 12A:
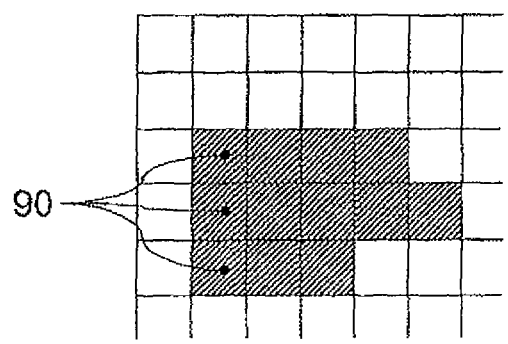
FIGS. 12(a) and 12(b) show in schematic fashion the basic principles of the pixel-by-pixel threshold comparison and of the determination of the 2-dimensional areas of variation from the difference images.

Returning to the result in FIG. 11(c), it can be found that noise can also occur in the difference images because of limited local resolution, scattering, and other noise effects. For this reason, a recognition algorithm can be applied first, which decides whether a significant gray-scale value variation is present. For this purpose, each pixel is first checked to see whether a certain threshold value for positive gray-scale value differences or a negative threshold value for negative gray-scale value differences has been exceeded. The pixels 90 above the threshold in our exemplary embodiment are shown in FIG. 12(a). The threshold values are to be determined by appropriate noise value determination methods for the individual x-ray system. The dependence of the threshold values on the x-ray parameters being used (mAs, kV) is also taken into account in the noise value determination procedure.

Figure 12B:
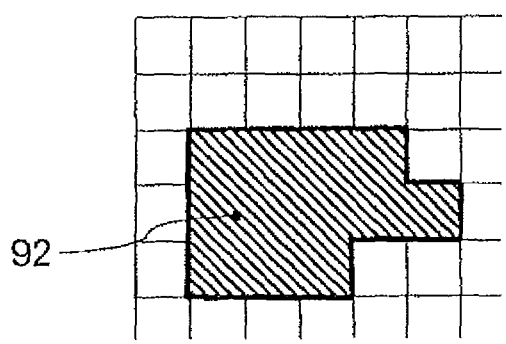

Next, areas of connected pixels 90 which comprise a gray-scale value variation above the threshold value are determined. These areas are called "2-dimensional areas of variation" 92 in the following (see FIG. 12(b)). Here the clinical user can determine the sensitivity to the size of such 2-dimensional areas of variation 92 by defining a minimum number of connected pixels 90 for such area or by specifying the size of the covered surface area in the form of a minimum width and a minimum height.

Figure 13A:
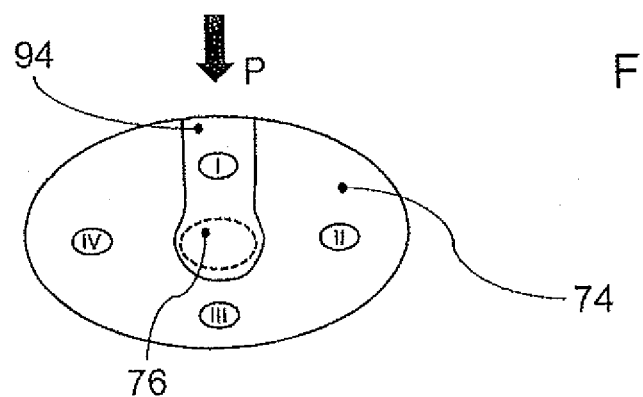
FIGS. 13(a)-13(c) show in schematic fashion the basic principles of the position-related relevance inspection of the density variation on which the 2-dimensional areas of variation are based.
Figure 13B:
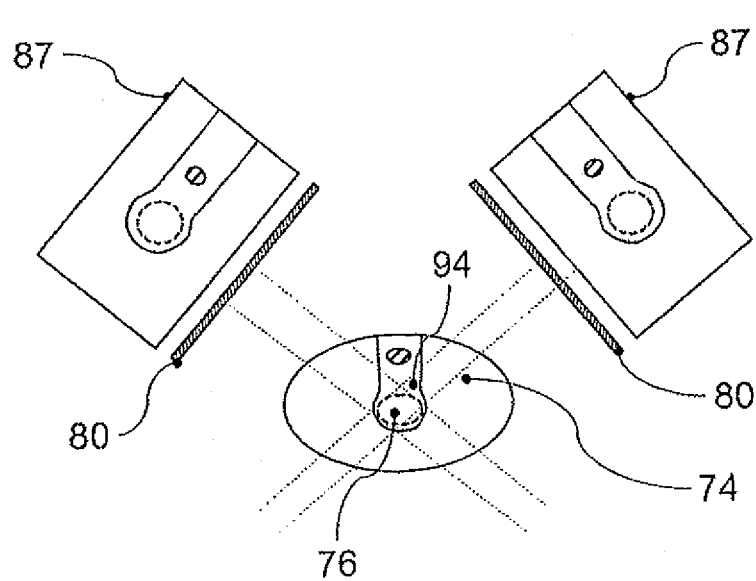

In the next step of the process, the system recognizes whether the density variation on which the determined 2-dimensional area of variation 92 is based lies in the relevant projection area of the proton beam for the planned irradiation field and is therefore able to contribute to a variation in the range in the first place. This type of identification cannot be made on the basis of one projection direction, for which reason the invention always provides a second projection direction. FIG. 13(a) shows a situation in schematic form. What is shown is a schematic diagram of a cross section through the patient 74 with the target area 76 for proton irradiation. Also shown are the beam projection area 94 and the possible positions I, II, III, and IV of density variations. With the help of the previously described DICOM structure sets for the target area, at-risk organs, other structures, and the isodose areas, these structures can now be projected appropriately into the difference images 87. This is shown schematically in FIG. 13(b).

Figure 13C:
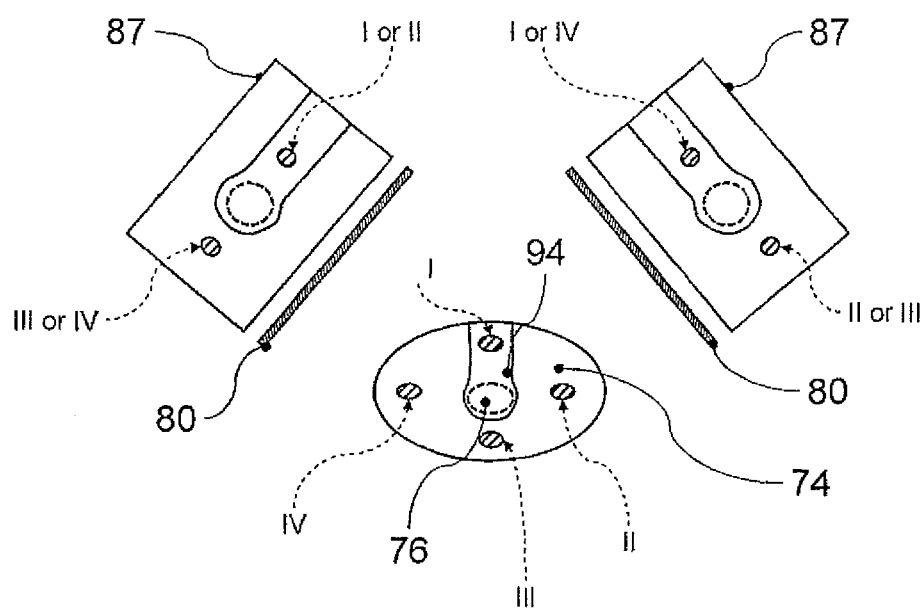

The density variation on which the identified 2-dimensional areas of variation 92 are based is now assigned spatially on the basis of the evaluation of its localization in the two projection directions. FIG. 13(c) shows the possible difference images 87 in the two projection directions and a table, in which, for each possible position I, II, III, and IV of the density variation in the patient 74, an "x" is entered if this density variation can lie in the projection area 94 or an "o" if it cannot. By superimposing the information of the two projection directions on each other, in the present case the result is obtained that only in position I the two projection directions suggest a possible relevance, whereas positions II, II, and IV can be excluded as of no relevance, because the density variation at these points is unimportant with respect to the analysis of range changes.

The system just described can display this information visually for the clinical user in the two difference images 87, in that, for example, the 2-dimensional areas of variation 92 are outlined in different colors to indicate relevance or lack thereof. The evaluation unit, however, can also simply mask out position-irrelevant 2-dimensional areas of variation 92 and exclude them from any further calculations.

For an accelerated evaluation of the range shift, the system described here then calculates the average gray-scale values in the areas of variation 92 which are relevant to range. What are determined are the average values for the two actual x-ray images 84 and the two nominal x-ray images 86. In each case, a noise correction determined for the specific system is carried out in the form of, for example, a subtraction. The result consists of four average gray-scale values, one for each of the four images.

Continuing from here, the system now determines the approximate spatial extent and spatial position of the density variation on which the relevant 2-dimensional areas of variation 92 are based. For this purpose, the 2-dimensional areas of variation 92 from the difference images 87 are back-projected into the 3-dimensional CT data set 32 of the patient's body.

Because this is done in 2 directions, what is obtained at the position $x_v$, $y_v$, $z_v$ is a body of intersection, called the "3-dimensional body of variation" 102 below (see FIG. 14). The coordinates for further description are established in such a way that the z-direction points in the direction of the long axis of the body while the patient is prone, and then x and y form a Cartesian coordinate system, wherein x lies in the horizontal plane. It is obvious that, in the x and y directions, only a rhombic area can be identified by back-projection of two images. The system described here therefore differentiates among several levels of detail, which can be selected by the clinical personnel in the situation at hand.

In the simplest case, the 3-dimensional shape of the body of variation 102 is modeled by simplifying the 2-dimensional areas of variation 92 into the form of rectangles with the average width and average length of the 2-dimensional areas of variation 92 and by the resulting intersections in the 3D volume. A polyhedron is obtained. This is sufficient to provide a very fast reconstruction and assessment of a possible range variation.

Figure 14:
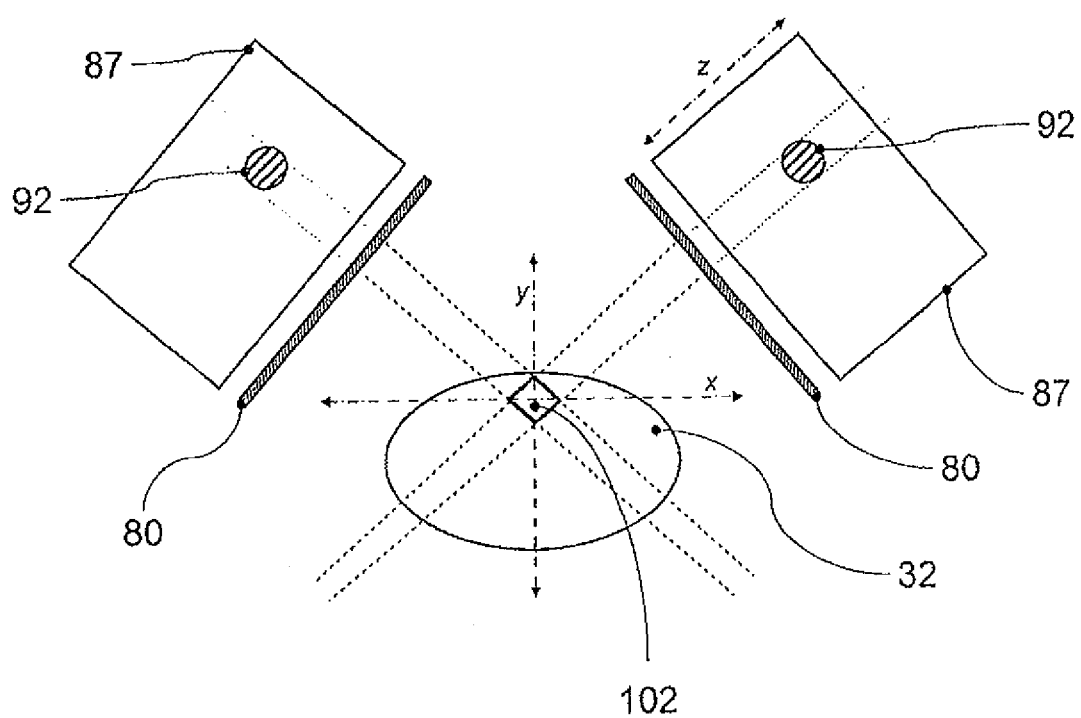
FIG. 14 is a schematic diagram of the back-projection of the 2-dimensional areas of variation into the 3-dimensional CT data set of the patient for forming the 3-dimensional body of variation.

The second level of approximation consists in that, under the assumption that in general there are no strictly polygonal structures in a human body, the cross-sectional surface shown in FIG. 14 is approximated by an ellipse, which represents a better approximation of anatomical structures. The longitudinal dimension is nevertheless determined from the average length in the z-direction of the 2-dimensional area of variation 92. As a result, what is obtained is a cylindrical volume in the 3D data set for the body of variation 102 having the density variation.

Another way in which the system can arrive at an approximation is by assuming elliptical contours in each of the two projections and in the image of the intersection, as a result of which a 3-dimensional ellipsoid is obtained.

The system also provides the possibility of arriving at an approximation by using the dimensions of the 2-dimensional areas of variation 92 actually present in the plane of intersection for each of the x,y projection intersection planes. By back-projecting for each z-position in the CT data set, a rhombic area is obtained as sketched in FIG. 14, but possibly with a different expanse for each z-position. This "stack" of rhombic areas then results in the 3-dimensional body of variation 102 by interpolation in the z-direction between the z-positions. The system also offers the possibility of approximating the above-described rhombic areas by ellipses, as a result of which a "sausage"-shaped volume is obtained for the 3-dimensional body of variation 102.

By means of additional projection directions, which the system also allows in principle, the contours can be determined more accurately, and thus the 3-dimensional form of the body of variation 102 can be described more effectively.

Now that the system has been provided with enough information, the actual density variation in the body of variation 102 can be found by solving a system of integral equations, and the effects on the range of the proton beams can be determined in the following steps of the process.

This system of integral equations can be solved numerically in all cases. The higher the degree of detail of the numerical solution desired, the larger the amount of computing work and time required.

At this point the complete 3D data set 32 from the computer tomography for the body section of the patient of interest is available to the system. This 3D data set 32 contains both the Hounsfield units distribution, the electron density distribution $\rho$ (x, y, z), and the corresponding assignment to the proton stopping power dE/dx (x, y, z, E). Also available are the identified position and dimensions of the body of variation 102 with the density variation in the patient's body and the decision whether or not the body of variation 102 lies in the projection area 94 of the proton beam field. The average gray-scale values of the identified 2-dimensional areas of variation 92 in the actual x-ray images 84 and in the nominal x-ray images 86 are also available for both projection directions.

Figure 15:
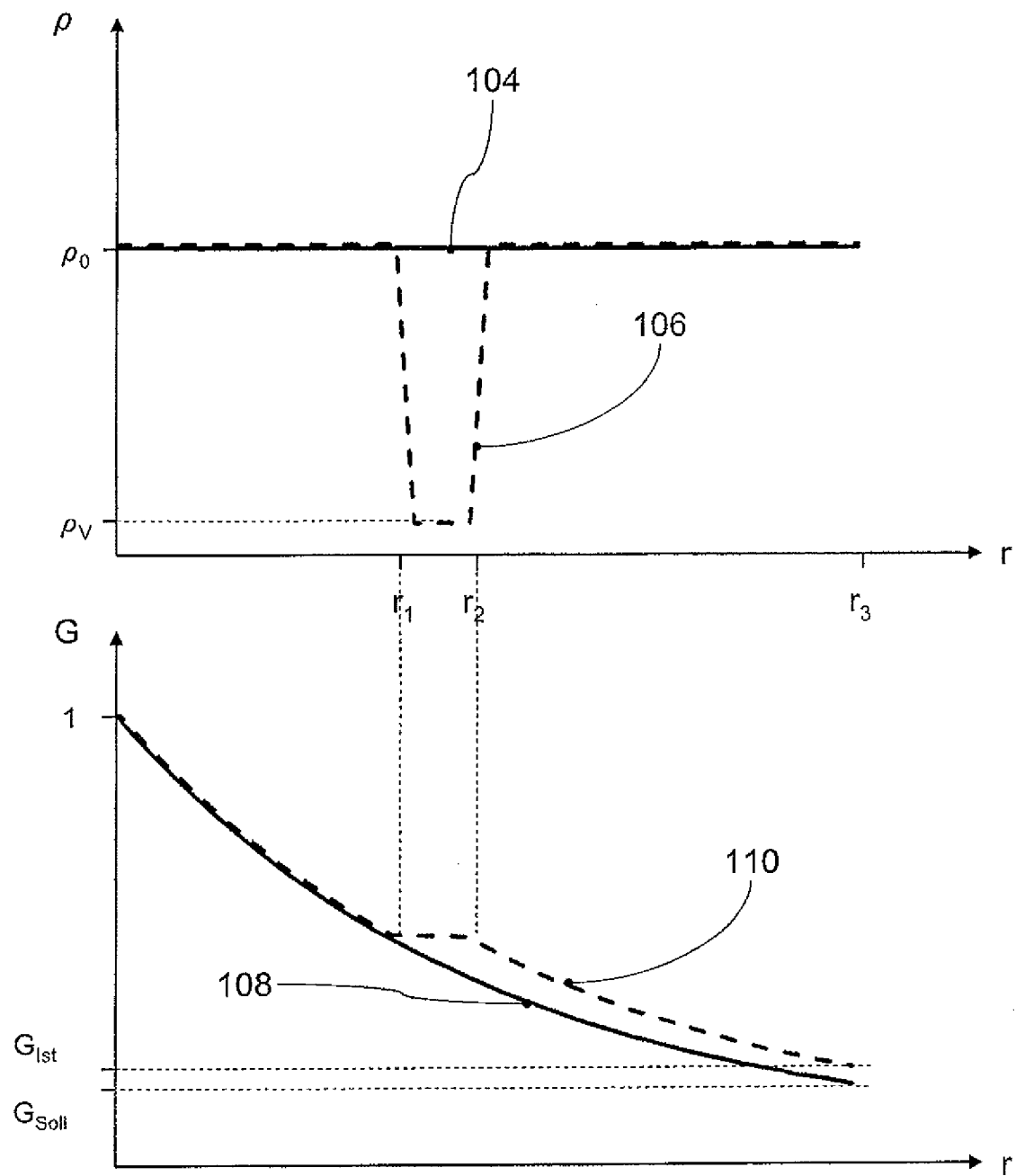
FIG. 15 is a schematic diagram of the relationship between gray-scale value and electron density on the basis of a simplified 1-dimensional example.

On the basis of this information, it is now possible, as sketched in FIG. 15, to set up and to solve a system of equations for each projection direction, wherein the solution of this system of equations represents the average electron density $\rho$ of the sought density variation. The fundamental relationship $$G(r) = e^{-\alpha \cdot \rho \cdot r}$$

is used for this purpose, where G is the numerical gray-scale value, $\alpha$ is a constant, and $\rho$ is the electron density.

In FIG. 15, this is shown to illustrate the simplest case of homogeneous density areas in one dimension. In the upper diagram of FIG. 15, the solid line 104 represents the case of a homogeneous electron density distribution, whereas the dashed line 106 represents the case of a homogeneous electron density distribution with a homogeneous body of variation 102. In the lower diagram, corresponding gray-scale value curves of the homogeneous case 108 and of the case 110 with the body of variation are shown in corresponding fashion.

The associated system of equations for this case can be sketched as follows, where "Soll"="nominal" and "Ist"="actual".

$$G_{Soll} = e^{-\rho_0 \cdot r_3}$$

$$G_{Ist} = e^{-\rho_0 \cdot r_1} \cdot e^{-\rho_v \cdot (r_2 - r_1)} \cdot e^{-\rho_0 \cdot (r_3 - r_2)}$$

$$\frac{G_{Soll}}{G_{Ist}} = g = e^{(\rho_0 - \rho_v)(r_1 - r_2)}$$

$$\Rightarrow \rho_v = \rho_0 + \frac{\ln g}{r_2 - r_1}$$

This simplified system can be generalized to all necessary dimensions and can be solved at least numerically.

In the process chain, the system has now determined the mean electron density value of the identified body of variation 102 with respect to location, shape, and size. On the basis of therapy planning and the basic calibrations for the specific system, it is now possible to determine directly the stopping power for proton beams and the distribution.

Figure 16:
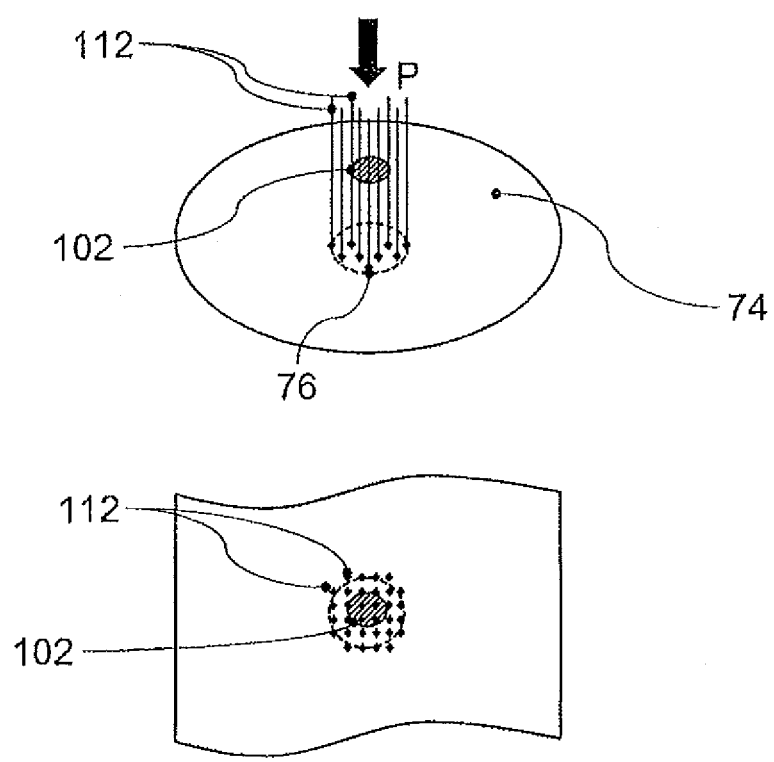
FIG. 16 is a schematic diagram of the determination of individual beams of the irradiation field which are affected by the density variation.

For this purpose, the system first identifies the individual beams 112 of the planned irradiation field affected by the density variation of the body of variation 102. FIG. 16 is a schematic diagram of the procedure. In cross section and in a top view in the proton irradiation direction, the identified body of variation 102 and the beam positions of the individual beams of the planned proton irradiation field and their original range are shown. Because the fluence matrix of the individual beams 112 is known from the therapy planning and was made available to the described system and because the 3-dimensional extent of the body of variation 102 is known, the system will, by simply determining the intersections of the individual beams 112 with the body of variation 102, identify the individual beams 112 which will penetrate through the body of variation 102 by virtue of their direction and the original range of which would at the same time have lain in or behind the area of the body of variation 102.

Figure 4A:
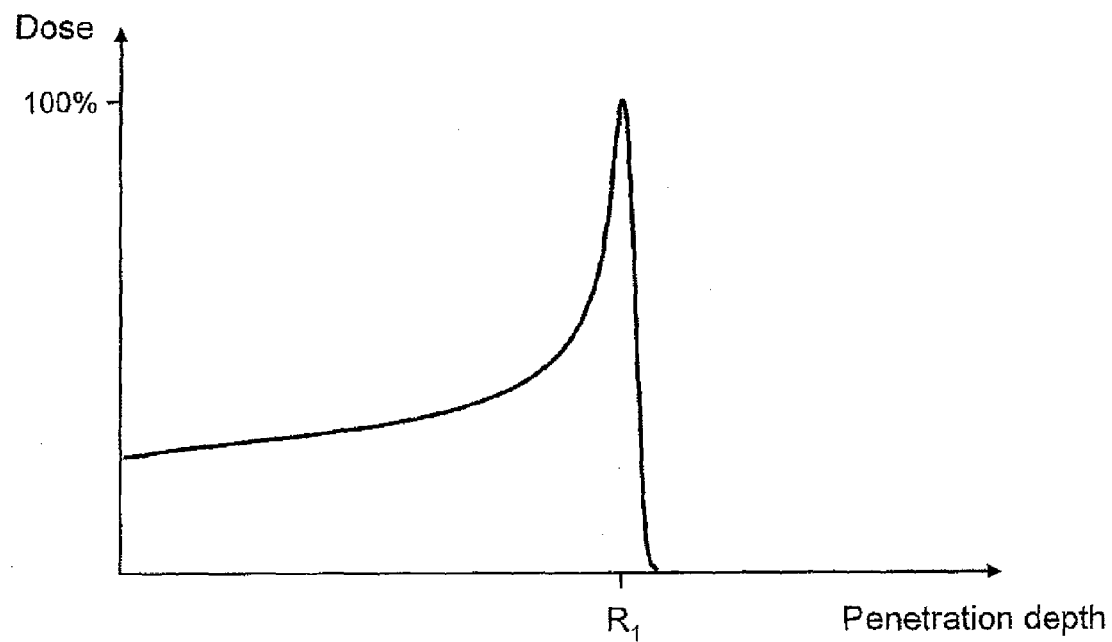
FIGS. 4(a) and 4(b) show the effect of a change in the range of a proton beam in matter of varying density.
Figure 4B:
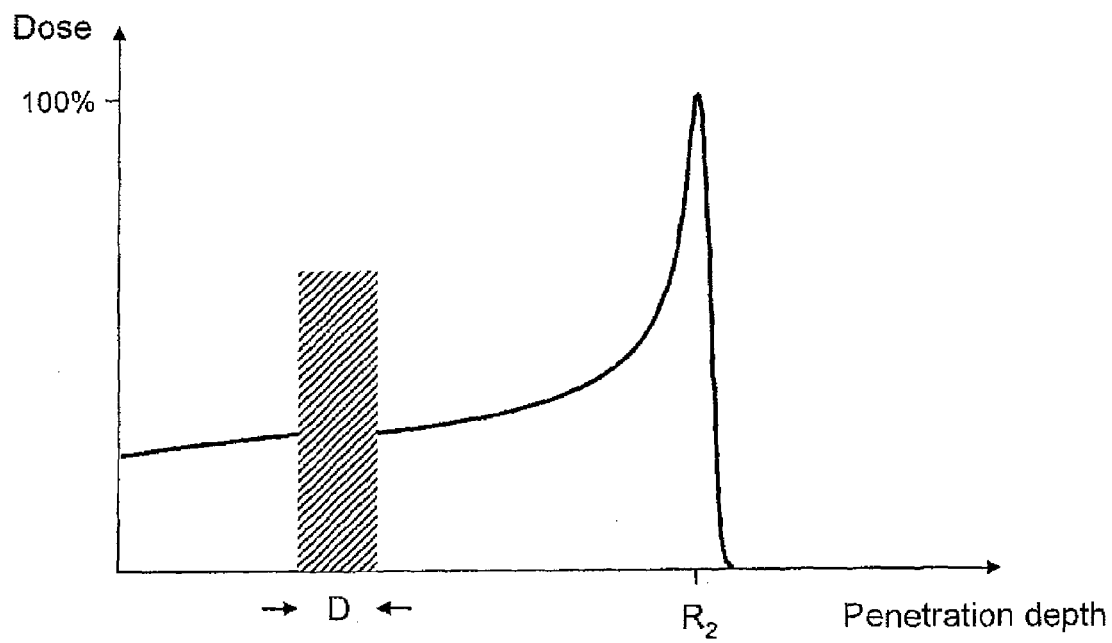

The system now knows the affected individual beams 112 of the original fluence matrix and the electron density in the body of variation 102. The system recalculates the range of each affected individual beam 112, the direction and position of which is known to the system. The range of the individual beam 112 is calculated in a manner similar to that used by the therapy planning system. In the area of the identified body of variation 102, however, the previous density distribution is replaced by the mean electron density now determined for this area. In the other areas of the body, the density distribution known from the CT data set 32 is used without change. The basic relationship between electron density and range of the proton beam can be seen in FIGS. 4(a) and 4(b).

The calibration method determined for the specific CT is used to convert the density values ρ(x) in the various voxels to the stopping power for proton beams dE/dx(x). The range R of the individual beam 112 is determined by way of its differential energy loss along its penetration path. The range along the individual beam direction is the integral over the energy-dependent differential energy loss until the energy of the individual beam 112 has been reduced to thermal energy values (<10 eV).

In the following equation, the basic relationship is shown for the homogeneous case (constant density value):

$$R = \int_{E_{therm}}^{E_0} \left(\frac{1}{\rho} \cdot \frac{dE}{dx}\right)^{-1} dE$$

where:
$E_0$=the initial energy,
$E_{therm}$=the final energy (≤10 eV),
ρ=the density in g/cm$^3$, and
dE/dx=the differential energy loss=stopping power in MeV/cm.

In the system described here, the range of the individual beams is determined numerically.

Figure 17A:
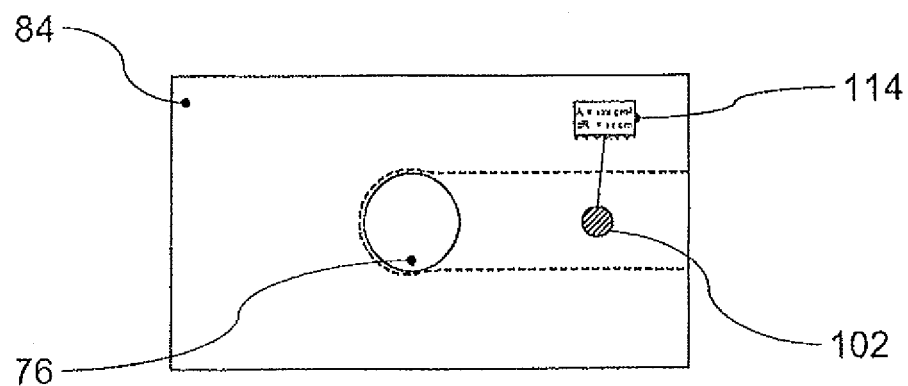
FIGS. 17(a)-17(c) show various ways in which information on the changes in the range of the irradiation field can be displayed.

The described system makes several display variants available to the clinical user, on the basis of which the clinical user can decide whether the identified range variation is clinically relevant or not:

(a) In a first display variant, sketched in FIG. 17(a), a simple warning message 114 is shown in the actual x-ray image 84 (and/or in the nominal x-ray image 86), in that the identified body of variation 102 is provided visually in the projection with the information on the mathematically estimated range variations in cm and the size of the range variation in cm$^2$. In this simple and very fast variant, it is possible to make use, if desired, of only those individual beams 112, which had the greatest original range at the location in question (x, y) of the irradiation field (distal edge), for these usually make the largest contribution to the dose and are associated with the most relevant clinical effects of a range variation.

Figure 17B:
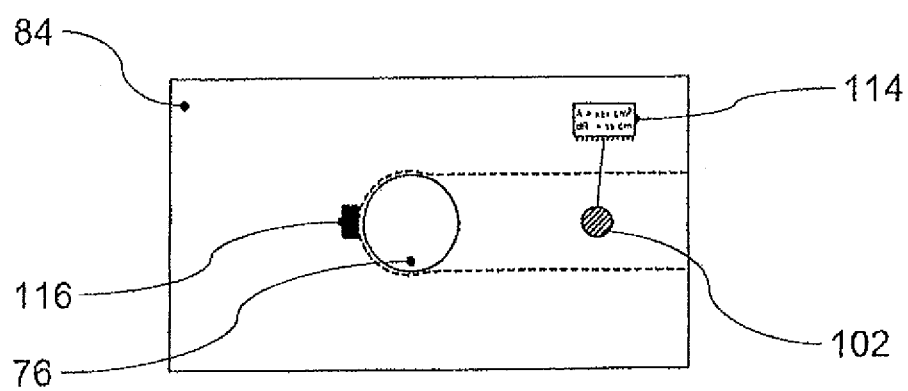
Figure 17C:
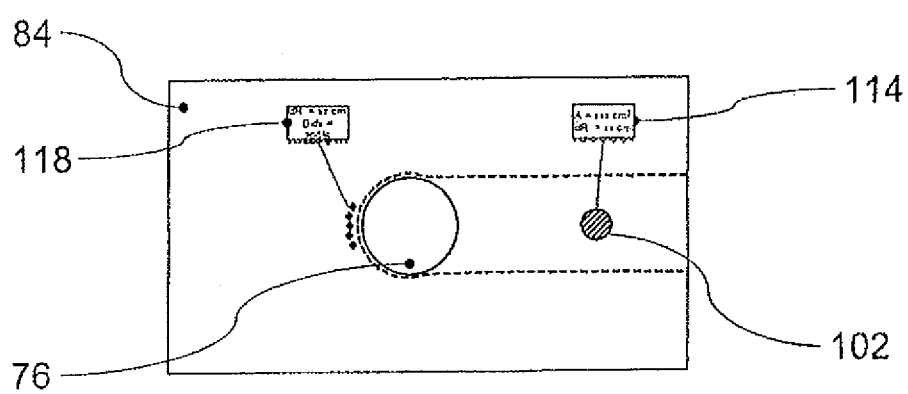

(b) In addition to display variant (a) described above, the area 116 which is subject to a range variation can be labeled or marked in color in the two actual x-ray images 84 (and/or the nominal x-ray images 86). This is shown schematically in FIG. 17(b) for the case of a range increase caused by a density variation in the proton irradiation area involving a decrease in density.

(c) In a more elaborate variant, the system calculates the range difference for each individual distal edge beam 112 used in the two above-described variants and displays their new range end-points in a manner similar to that of variant (b), but individually for each single beam 112, possibly with a magnification function, activated by selection of an individual beam 112. In addition, a weighting index can be shown in a field 118 for each of these individual beams 112, which index represents how large the contribution of this individual beam 112 is to the dose distribution in comparison with the average contribution of all individual beams 112. The clinical user of the system can base a more detailed decision on this information.

(d) Variant (c) is expanded to include a user-selectable number of energy layers instead of merely the deepest (distal edge) energy layer (not shown).

(e) By recalculating the range for all individual beams 112 of the entire fluence matrix and using a dose algorithm in a way similar to that of the therapy planning system, the system can, on its highest level of detail, calculate a new isodose distribution and display it in the two projection displays of the actual x-ray images 84 and/or the nominal x-ray images 86 (not shown).

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A method for identifying possible changes in a range of a planned irradiation field before a patient is irradiated with charged particles, comprising:
    conducting a computer tomography over at least a part of the patient to generate a 3-dimensional computer tomography data set;
    providing an x-ray system comprising two high-resolution x-ray detectors, which form an angle of 60-120° to each other, and two x-ray sources opposite the x-ray detectors, wherein each combination of an x-ray source and an x-ray detector defines one of two projection directions;
    preparing two actual x-ray images of at least a part of the patient in the two projection directions by means of the two x-ray detectors;
    calculating two digitally reconstructed nominal x-ray images from the computer tomography data set corresponding to the two projection directions of the x-ray system;
    conducting a difference analysis to determine differences between the actual x-ray image and the associated nominal x-ray image for the two projection directions;
    checking the relevance of the found differences with respect to spatial extent and with respect to localization in reference to the planned irradiation field and determining relevant 2-dimensional areas of variation;
    determining a 3-dimensional body of variation by back-projecting the two 2-dimensional areas of variation into the 3-dimensional computer tomography data set;

calculating a mean electron density of the 3-dimensional body of variation on the basis of the found differences between the actual x-ray image and the associated nominal x-ray image for the two projection directions;

identifying individual beams of the planned irradiation field which pass through the 3-dimensional body of variation;

calculating, under consideration of the changed electron density value in the 3-dimensional body of variation, prospective changed ranges of the identified individual beams of the planned irradiation field; and displaying or making available information on the calculated changed ranges.

2. The method of claim 1 wherein the step of conducting a difference analysis for determining differences between an actual x-ray image and an associated nominal x-ray image comprises the step of subtracting numerical gray-scale values of pixels of the nominal x-ray image from numerical gray-scale values of corresponding pixels of the actual x-ray image to determine a pixel-by-pixel gray-scale value deviation.

3. The method of claim 2 wherein, before the step of pixel-by-pixel subtraction of the numerical gray-scale values, a gray-scale value matching is carried out between the actual x-ray images and the nominal x-ray images.

4. The method of claim 3 wherein the gray-scale value matching between the actual x-ray image and the nominal x-ray image comprises the step of applying, in an iterative numerical optimization process, a matching function for matching a gray-scale value frequency curve of the actual x-ray image to a gray-scale value frequency curve of the nominal x-ray image.

5. The method of claim 3 wherein, before the gray-scale value matching between the actual x-ray image and the nominal x-ray image, a resolution of the one of the actual x-ray image and the nominal x-ray image having the lower resolution is increased to match the higher resolution of the other one of the actual x-ray image and the nominal x-ray image.

6. The method of claim 2 wherein, for determining the relevant 2-dimensional areas of variation, only areas are considered which consist of a predetermined minimum number of connected pixels which, after the step of subtracting the numerical gray-scale values of the pixels of the nominal x-ray image from the numerical gray-scale values of the corresponding pixels of the actual x-ray image, show a gray-scale value deviation above a predetermined threshold value.

7. The method of claim 2 wherein the gray-scale values are averaged over the pixels of each relevant 2-dimensional area of variation.

8. The method of claim 1 wherein each relevant 2-dimensional area of variation is graphically highlighted in the actual x-ray images or in the nominal x-ray images.

9. The method of claim 1 wherein, before back-projecting the relevant 2-dimensional areas of variation into the 3-dimensional computer tomography data set, the 2-dimensional areas of variation are simplified to rectangles with an average width and average length of the associated 2-dimensional area of variation.

10. The method of claim 1 wherein, for calculating the average electron density of the 3-dimensional body of variation, systems of equations for each of the two projection directions based on x-ray attenuation relationship $$G(r)=e^{-\alpha \cdot \rho \cdot r}$$

are solved numerically, wherein G is the numerical gray-scale value, and ρ is the electron density.

11. The method of claim 1 wherein calculating the prospective changed ranges of the identified individual beams of the planned irradiation field comprises the steps of determining the differential energy loss along a penetration path of the individual beam and determining a range of the penetration path of the individual beam by integration over the energy-dependent differential energy loss.

12. The method of claim 1 wherein calculating the prospective changed ranges of the identified individual beams of the planned irradiation field is limited to only the individual beams with longest original ranges.

13. The method of claim 1 wherein displaying information on the calculated changed ranges comprises the step of displaying the information visually in the actual x-ray images or nominal x-ray images as data on an extent of range change.

14. The method of claim 1 wherein displaying information on the calculated changed ranges comprises the step of marking in color a range variation in a distal terminal region of the irradiation field in the actual x-ray images or nominal x-ray images.

15. The method of claim 1 wherein displaying information on the calculated changed ranges comprises the steps of calculating a changed dose distribution which results from the calculated changed ranges, and of displaying projections of isodose areas of the changed dose distribution in the two actual x-ray images or nominal x-ray images.

16. The method of claim 1 wherein the two high-resolution x-ray detectors form an angle of 75-105° to each other.

* * * * *